US007323508B2

(12) United States Patent
Orchison et al.

(10) Patent No.: US 7,323,508 B2
(45) Date of Patent: Jan. 29, 2008

(54) NEUTRAL CARBONATED ALKALINE EARTH METAL CARBOXYLATES

(75) Inventors: Jack James Angus Orchison, Leigh (GB); Malcolm Thomas John Mellor, Bolton (GB)

(73) Assignee: Akzo Nobel N.V., Arnhem (NL)

( * ) Notice: Subject to any disclaimer, the term of this patent is extended or adjusted under 35 U.S.C. 154(b) by 270 days.

(21) Appl. No.: 10/493,791

(22) PCT Filed: Nov. 14, 2002

(86) PCT No.: PCT/EP02/12759

§ 371 (c)(1),
(2), (4) Date: Jun. 10, 2004

(87) PCT Pub. No.: WO03/045887

PCT Pub. Date: Jun. 5, 2003

(65) Prior Publication Data

US 2004/0254279 A1    Dec. 16, 2004

(30) Foreign Application Priority Data

Nov. 28, 2001   (EP) .................................. 01204591

(51) Int. Cl.
*C08F 2/08* (2006.01)
(52) U.S. Cl. ........................ 524/396; 524/400; 524/543

(58) Field of Classification Search ................ 524/396, 524/400, 543
See application file for complete search history.

(56) References Cited

U.S. PATENT DOCUMENTS

| 4,665,117 A | 5/1987 | Quinn |
| 4,925,883 A | 5/1990 | Baker |
| 5,830,935 A | 11/1998 | Khattar et al. |

FOREIGN PATENT DOCUMENTS

| EP | 0 248 465 A1 | 12/1987 |
| EP | 0 267 658 A2 | 5/1988 |
| EP | 0 279 493 A2 | 8/1988 |
| EP | 0 282 912 A2 | 9/1988 |
| EP | 0 298 572 A1 | 1/1989 |
| EP | 0 373 484 A1 | 6/1990 |
| EP | 0 437 886 A2 | 7/1991 |
| JP | A 59-105043 | 8/1982 |
| WO | WO 96/15186 | 5/1996 |
| WO | WO 97/00907 | 1/1997 |
| WO | WO 97/00908 | 1/1997 |
| WO | WO 97/17400 | 5/1997 |
| WO | WO 97/47578 | 12/1997 |

*Primary Examiner*—Peter D. Mulcahy
(74) *Attorney, Agent, or Firm*—Kenyon & Kenyon LLP

(57) ABSTRACT

The invention relates to carbonated alkaline earth metal carboxylates that are neutral, meaning they have a base value of less than 10 mg KOH/g, and that are derived from a mixture of, preferably branched, optionally cyclic, $C_4$-$C_{40}$ alk(en)yl carboxylic acids and $C_6$-$C_{30}$ alkaryl or aralkyl carboxylic acids. Also a process to make such products is claimed, as well as the use of the products to stabilize PVC.

4 Claims, No Drawings

NEUTRAL CARBONATED ALKALINE EARTH METAL CARBOXYLATES

The present invention relates to alkaline earth metal carboxylates that are neutral, meaning they have a base value of less than 10 mg KOH/g, a process to make them, and their use as a stabilizer for poly vinyl chloride.

Alkaline earth metal carboxylates and their use in poly vinyl chloride (PVC) are well known. EP-A-0 282 912, for instance, discloses PVC stabilizers that are a mixture of a specific alcohol, isocyanurate, and a specific ratio of a zinc-salt and one or more alkaline earth metal carboxylates derived from an aliphatic, aromatic, or aromatic-aliphatic $C_7$-$C_{18}$ carboxylic acid. Similarly, WO 96/15186 discloses PVC stabilizers that are mixtures of specific organic acid phosphites, specific organic triphosphites, and a mixture of Ba and Zn carboxylates of a mixture of $C_6$-$C_{20}$ alk(en)yl and $C_8$-$C_{10}$ aromatic carboxylic acids. WO 97/00907 discloses a process to make a mixture of Ca and/or Mg and Zn carboxylates of a mixture of $C_{16}$-$C_{30}$ alk(en)yl carboxylic acid and benzoic acid. EP-A-0 279 493 discloses specific carbonated alkaline earth metal carboxylates derived from blends of a $C_8$-$C_{30}$ alkyl salicylic acid and branched $C_4$-$C_{40}$ alkyl carboxylic acids and their use in lubricating oils and fuel compositions. The products of this reference are not neutral but "overbased", meaning that a less than stoichiometric amount of acid, acid being the total of carboxylic acids and $CO_2$, has reacted with the metal (hydr)oxide. It is noted that the "base index" as used in EP-A-0 279 493 is the ratio of alkaline(earth) metal to organic acid which cannot be equated to the base value as used in this document.

The conventional products were found not to be satisfactory. More particularly, there still is a need for alternatives and improved products in the field of PVC stabilizing. The new products should be effective stabilizers that can be produced more cost efficiently at equal alkaline earth metal content and without the necessity to use alkylphenols, that are stable upon storage, and that do not emit volatile matter during processing or use.

Surprisingly, we found that alkaline earth metal carboxylates that are neutral, meaning they have a base value of less than 10 mg KOH/g, derived from a mixture of, preferably branched, optionally cyclic, $C_4$-$C_{40}$ alk(en)yl carboxylic acids and $C_6$-$C_{30}$ alkaryl or aralkyl carboxylic acids were effective stabilizers for polymers, particularly PVC. They can be produced more cost-efficiently than conventional alkaline earth metal carboxylates with the same alkaline earth metal content and without that environmentally suspect alkyl phenols are used. The products were storage-stable for a period of at least three months without the formation of gels or solids. Preferably, the neutral alkaline earth metal carboxylates according to the invention have a base value of less than 9 mg KOH/g, more preferably less than 7.5 mg KOH/g, more preferably less than 5 mg KOH/g, most preferably less than 3 mg KOH/g. Preferably, the base value is 0 mg KOH/g or more.

For the neutral carbonated alkaline earth metal carboxylates according to the invention to be effective, the alkaline earth metal content is to be as high as possible. Preferably, the alkaline earth metal content in the final product is above 10 percent by weight, based on the weight of all carbonated alkaline earth metal carboxylates (% w/w). More preferably, the amount of alkaline earth metal in the product is more than 12.5% w/w, even more preferably greater than 17.5% w/w, while an amount of greater than 25% w/w is most preferred. It is to be understood that for Ba-based neutral carbonated alkaline earth metal carboxylates, because of the higher molecular weight of the Ba, the preferred weight percentages are even higher. More specifically, in such products the Ba content is preferably greater than 25% w/w, more preferably greater than 30% w/w, most preferably more than 35% w/w. However, if so desired, and independent of what alkaline earth metals are used, the product can be diluted with one or more further conventional diluents, such as plasticizers, or fillers to facilitate the incorporation into a PVC formulation. Preferably, the products are liquid, but if formulated with e.g. fillers, they can also be used in the paste or solid form.

Preferably, the products according to the invention do not comprise a moiety derived from an alkyl phenol, such as octylphenol, nonylphenol, and dodecylphenol.

In the neutral carbonated alkaline earth metal carboxylates according to the invention, one or more alkaline earth metals can be used. Preferred are calcium and barium. Typically, the alkaline earth metal is introduced in the reaction by addition of the hydroxide or oxide of the metal.

The (cyclic) $C_4$-$C_{40}$ alk(en)yl carboxylic acids that are used are preferably selected from the group of oleic acid, ethylhexanoic acid, iso $C_8$-$C_{10}$ acids, as supplied by ExxonMobil as Cekanoic® acids, versatic acids, as disclosed in EP-A-0 279 493, hydroxyacids, such as lactic acid, naphthenic acid, and mixtures thereof. More preferred are acids selected from oleic acid, ethylhexanoic acid, iso $C_8$-$C_{10}$ acids, and versatic acids.

The $C_6$-$C_{30}$ alkaryl or aralkyl carboxylic acids are preferably selected from benzoic acid, derivatives of benzoic acid where the benzoic ring has been substituted, such as in tert.butyl benzoic acid and toluic acid, salicylic acid, naphthalic acid, and derivatives of naphthalic acid where the benzoic ring has been substituted. Most preferred are the benzoic and naphthalic acids and their derivatives.

The amount and ratio wherein the alk(en)yl carboxylic and alkaryl or aralkyl carboxylic acid is to be used is not critical. The total amount of carboxylic acid to be used is less than stoichiometric. Preferably, the ratio of alk(en)yl carboxylic to alkaryl and/or aralkyl carboxylic acid is at most 20:1. More preferably, this ratio is at most 10:1 and most preferred is a ratio of at most 8:1. Preferably, the ratio of alk(en)yl carboxylic to alkaryl and/or aralkyl carboxylic acid is at least 1:10, more preferably at least 1:1, and most preferably at least 3:1.

The reaction mixture of carboxylic acids, alkaline earth metal (hydr)oxide, and optional solvent(s) is herein referred to as the initial reaction mixture. Preferably, the amount of alkaline earth metal (hydr)oxide is less than 20, preferably less than 10 equivalents per equivalent carboxylic acid that is used. As said, the amount of alkaline earth metal (hydr) oxide is more than 1 equivalent per equivalent carboxylic acid that is used. The carboxylic acids and alkaline earth metal (hydr)oxide is reacted in a conventional way, generally at temperatures from 80 to 180° C., preferably 90-160° C., and typically the reaction is driven to completion by (simultaneous) removal of water.

The carbonation and neutralization of the resulting alkaline earth metal carboxylates is preferably effected by contacting them with $CO_2$. However, also other conventional ways of carbonation may be used. As said, the product is defined to be neutral if the base value is less than 10 mg KOH/g. Preferably, the base value is less than 7.5 mg KOH/g, more preferred is a base value of 5 mg KOH/g. Most preferred are base values less than 3 mg KOH/g. It is noted that the base value will be greater than or equal to 0.

During the carbonation with $CO_2$, preferably use is made of a promoting solvent, meaning that a solvent is used comprising an alcohol and/or alkoxylated compounds. Alkyl phenols can be used for this purpose, but, as said, are less desired. Preferred alcohols include saturated and unsaturated, linear and branched alkyl alcohols with 6 to 18 carbon atoms. Suitable alcohols are hexanol, 2-ethylhexanol, oleylalcohol and 2-(2-butoxyethoxy)ethanol, which is also known as butyldioxitol. Suitable alkoxylated compounds include alkoxylated phenols. Preferred are ethoxylated and/or propoxylated $C_1$-$C_{18}$ alcohols. Conveniently, a commercial mixture of alcohols with a varying degree of alkoxylation is used. Favourable results have been obtained using a mixture of one or more alcohols and one or more alkoxylated compounds. Without wishing to be bound to this theory, it is believed that the promoting solvent (mixture) stabilises a desirable micellar structure in the carbonation reaction. For preferred Ba-containing carbonated compounds, most preferably a mixture of ethylhexanol and either butyldioxitol or $C_{12}$-$C_{15}$ ethoxylates or phenol ethoxylates is used.

Preferably, the promoting solvent is present in the carbonation process in an amount of at least 5% w/w, preferably at least 10% w/w of the initial reaction mixture. For economic reasons, the total amount is less than 50% w/w. More preferably, the promoting solvent is chosen such that at least 2% w/w of the initial reaction mixture of the carbonation process is an alcohol, while at the same time at least 6% w/w of the alkoxylated compounds is present. Most preferably, at least 4% w/w of alcohol and 12% w/w of alkoxylated compounds are present in said initial reaction mixture. With the use of such promoting solvents, a reaction temperature of 150-160° C. is conveniently used. The $CO_2$ is simply passed through the solution so that it reacts with the alkaline earth metal carboxylates. The rate at which the $CO_2$ is to be dosed depends on the reactor geometry.

In a preferred embodiment of the invention, (part of) the promoting solvent is recycled from any step after the carbonation reaction step back into said carbonation step or other steps preceding it.

In the whole process a conventional solvent for the carboxylic acid, alkaline earth metal carboxylates, and carbonated alkaline earth metal carboxylates can be used. Typically, such solvents are hydrocarbons. Good results have been obtained using paraffins, such as Marcol®52 ex ExxonMobil, naphthenic hydrocarbons, such as Catenex® S321 ex Shell, and alkyl esters of oleic and/or tallow acid. If such oleates and tallates are used as a solvent, they are preferably used after the carbonation step. Especially if the promoting solvent is recycled in the process, the oleates and tallates are pre-eminently suited to be introduced when the promoting solvent is removed. Preferably, the amount of conventional solvent that is used is at least 10% w/w of the initial reaction mixture.

If (part of) the promoting solvent and, if used, the conventional solvent, remains in the final product, it is preferred that these solvents have a boiling point of at least 280° C. and a flash point of at least 105° C. in order to ensure a safe handling of the products. The amount of volatiles emitted during processing, handling, and use of a resin, preferably PVC, containing the product of the invention was found to be minimized when such solvents are present in the final product. In the process according to the invention the carbonation step can be followed by said optional promotion solvent removal and/or recycle step, and optionally one or more of the conventional solvents can be added. The final product preferably contains less than 1%, preferably less than 0.5%, of water. In order to achieve this water content, the water is to be removed during the initial reaction of alkaline earth metal (hydr)oxide and carboxylic acid, or it can be removed in a further drying step after the initial reaction step. Conventional aging steps can be refrained from in the present process.

Typically, the neutral carbonated alkaline earth metal carboxylates are used as part of a liquid stabilizer system for PVC. Suitably, they are present in such a stabilizer system at a level of at least 5% w/w, preferably at least 10% w/w. However, no more than 50% w/w, 40% w/w. The liquid stabilizer system is typically used in an amount of 1-4 parts by weight, preferably 1.5-3 parts by weight, based on 100 parts by weight of resin. However, the products according to the invention can also be formulated with other chemicals before they are introduced into the resin.

It is noted that the base value of the product is measured in the conventional way by dissolving about 3 g (weight, g) of the product in a mixture of 50 cc toluene and 50 cc isopropanol. The ratio of solvents can be changed if this improves the solubility of the sample. Phenolphthalein indicator is added and the mixture is titrated (volume, ml) with about 0.1M (titre, mole/l) aqueous HCl till the colorless end point. The base value (mgKOH/g)=volume×titre×56.1/weight.

It is furthermore noted that the term PVC is meant to denominate compositions comprising any honmopolymer or copolymer comprising units derived from vinyl chloride. The term includes chlorinated vinyl chloride polymers. Most preferred are conventional PVC grades, typically comprising more than 90% vinyl chloride, as are obtainable by mass, suspension, micro-suspension, and emulsion polymerization processes. These most preferred vinyl chloride (co)polymers include conventional flexible, semi-rigid and rigid grades of PVC.

Optionally the PVC comprises one or more conventional adjuvants employed to facilitate processing or to enhance the properties of the end product. Examples of such optional adjuvants include heat stabilizers, colour stabilizers, acid-scavengers, organophosphite esters, anti-oxidants, ultraviolet absorbers, antistatic agents, lubricants, flame retardants, plasticizers, flow and impact modifiers, fillers, and pigments.

The invention is elucidated by the following examples.

EXAMPLES 1-5

A conventional Dean and Stark apparatus, equipped with a stirrer, was charged with 67.5 g butyldioxitol, 50.0 g dodecylbenzene, 50.0 g 2-ethylhexanol, 64.5 g $C_{10}$-tertiary carboxylic (versatic) acids, 26.5 g oleic acid, and 11.4 g benzoic acid. After heating under nitrogen to a temperature of 90° C., 119.1 g barium hydroxide monohydrate was added such that the temperature remained below 100° C. Thereafter vacuum was applied (150 mmHg) and the reaction mixture was heated till 150-160° C. When the reaction was finished (no water being distilled off), $CO_2$ was passed through the solution at a rate of 0.5 l/min until the base value was less than 3 mgKOH/g. Near the end of the reaction the $CO_2$ was no longer absorbed/reacted. During the carbonation, some water is formed that largely distilled from the reaction mixture. However, to further dry the product and to remove 2-ethylhexanol, the product was submitted to further vacuum-distillation in the conventional way. A total of 26.0 g of $CO_2$ had been used, some of which had not reacted.

The product was filtered through Dicalite® 478 ex Dicalite-Europe to give a clear amber liquid with a Ba-content of 27%, and a base value of less than 3, at a yield of 98%.

In example 2 the above experiment was repeated except that a hydrogenated paraffin solvent Shellflex®2210 ex Shell (or Catenex® S321) was used instead of the dodecylbenzene. The same results were obtained.

In example 3, example 1 was repeated except that an ethoxylated $C_{12}$-$C_{15}$ alcohol with, on average, 3 EO units per molecule, was substituted for the butyldioxitol. The Ba content of the neutral clear product was 26.6% w/w.

In example 4, example 1 was repeated except that ethoxylated phenol with, on average, 4 EO units per molecule was used instead of the butyldioxitol. Again a neutral and clear product was obtained with a Ba content of 26.6% w/w.

In example 5 a neutral product with an even higher Ba content was produced by repeating the procedure of example 1 but wherein a total of 166.7 g of the barium hydroxide monohydrate was used. The final product had a Ba content of 32.3% w/w. More $CO_2$ had reacted before a neutral compound was obtained.

In example 6, a higher boiling solvent such as 2-ethylhexyl oleate could partially replace the butyl dioxitol of example 1. For example by using 33.75 g butyl dioxitol and 83.75 g 2-ethylhexanol and adding 33.75 g of, for example, 2-ethylhexyl oleate after the carbonation but before the distillation of the 2-ethylhexanol.

In example 7, the procedure of example 1 was repeated except that after the carbonation step, a convenient amount of, for example, 2-ethylhexyl oleate was added before submitting the product to a distillation step at 160° C. at a pressure of 10 mmHg to distil off the requisite amount of butyl dioxitol.

In examples 6 and 7, products with reduced volatility were obtained for which the heat stability results were unimpaired.

COMPARATIVE EXAMPLES A-C

In example A, the procedure of example 1 was repeated, except that 48.0 g of dodecylbenzene was used (instead of 50.0 g) and that 13.5 g of iso $C_8$ acid (supplied as a Cekanoic® acid ) was used instead of the benzoic acid. Hence, all acids were aliphatic in nature.

In examples B and C commercial Ba-containing compounds Plastistab® 2106 and Plastistab® 2508, respectively, were evaluated. Both are supplied by OMG. Plastistab® 2106 is a carbonated Ba alkylphenolate containing about 28% w/w of Ba and a base value of about 26 mgKOH/g, while Plastistab® 2508 is a carbonated Ba carboxylate/alkylphenolate with a Ba content of about 34% w/w and a base value of about 12 mgKOH/g.

In order to evaluate the performance of some of the compositions presented above, the following generic liquid stabilizer formulations were made by combining:

|  | Example | | | | |
| --- | --- | --- | --- | --- | --- |
|  | A' | B' | C' | 1' | 3' |
| Basic Zn-octoate | 8 | 8 | 8 | 8 | 8 |
| Di-isodecylphenylphosphite | 45.46 | 46.60 | 50.82 | 45.41 | 45.31 |
| Diphenyl phosphite | 2 | 2 | 2 | 2 | 2 |
| Dehydroacetic acid | 2.5 | 2.5 | 2.5 | 2.5 | 2.5 |
| Butoxyethoxyethanol | 10 | 10 | 10 | 10 | 10 |
| Butylated hydroxytoluene | 5 | 5 | 5 | 5 | 5 |
| 2-ethylhexanoic acid | 2 | 2 | 2 | 2 | 2 |
| Ba-compound of example | A | B | C | 1 | 3 |
| Amount used | 25.04 | 23.90 | 19.68 | 25.09 | 25.19 |

The blend was heated to 60° C. while stirring to give a homogeneous liquid, which was filtered before further use.

The liquid stabilizers were evaluated in the following flexible PVC recipe:

| Suspension PVC (K64) | 100 parts by weight, |
| --- | --- |
| Di-2-ethylhexyl phthalate | 45 parts by weight, |
| Lankroflex ® E 2307 | 3 parts by weight, |
| Liquid stabilizer | 2 parts by weight. |

Lankroflex® 2307 is epoxidized soy-bean oil as supplied by Akzo Nobel (Akcros).

The components were mixed by hand and subsequently milled into sheets using a 2-roll heated mill with a roll diameter of 110 mm, roll temperature of 165 and 161° C., a front roll speed of 26.6 rpm, a friction ratio of 1:1.10, and a nip setting of 0.5 mm. The time that the mixture was on the rolls was 3.0 minutes. The sheets were cut into strips with a size of 410×20 mm and placed in a test oven with a temperature of 185° C. The Yellowness Index (YI) of the strips was determined in accordance with official test method BS 2782: Part 5, Method 530A, after the stripd had been in the oven for the indicated period of time. The results are summarized below.

|  | Example | | | | |
| --- | --- | --- | --- | --- | --- |
|  | A" | B" | C" | 1" | 3" |
|  | Liquid stabilizer of example | | | | |
|  | A' | B' | C' | 1' | 3' |
| Time (minutes) | Yellowness Index | | | | |
| 0 | 6.4 | 6.6 | 6.0 | 5.7 | 5.9 |
| 8 | 7.2 | 6.8 | 6.2 | 6.0 | 6.1 |
| 16 | 8.1 | 7.7 | 7.0 | 7.0 | 7.0 |
| 24 | 10.3 | 8.9 | 8.4 | 8.2 | 8.0 |
| 32 | 10.7 | 9.9 | 9.6 | 9.7 | 9.1 |
| 40 | 11.2 | 11.0 | 11.3 | 10.7 | 9.8 |
| 48 | 11.4 | 13.2 | 12.3 | 10.8 | 10.7 |

The products according to the invention outperform conventional products with respect to early color and color-hold.

The liquid stabilizers were also evaluated in the following semi-rigid PVC recipe:

| Suspension PVC (K71) | 100 parts by weight, |
| --- | --- |
| Di-2-ethylhexyl phthalate | 27 parts by weight, |
| Titanium dioxide | 5 parts by weight, |
| Lankroflex ® E 2307 | 3 parts by weight, |
| Liquid stabilizer | 2 parts by weight. |

The recipes were mixed by hand and subsequently milled into sheets and tested as presented in the previous examples except that the nip setting of the mill was 0.4 mm.

The results are summarized below.

| Time (minutes) | Liquid stabilizer of example | | | | |
|---|---|---|---|---|---|
| | A" | B" | C" | 1" | 3" |
| | A' | B' | C' | 1' | 3' |
| | Yellowness Index | | | | |
| 0 | 3.8 | 3.9 | 3.2 | 3.2 | 3.2 |
| 8 | 4.7 | 4.3 | 4.0 | 4.0 | 4.0 |
| 16 | 7.0 | 7.0 | 7.2 | 5.9 | 6.0 |
| 24 | 9.1 | 12.0 | 12.4 | 8.9 | 9.0 |
| 32 | 10.9 | 13.3 | 16.0 | 10.1 | 9.8 |
| 40 | 11.4 | 13.6 | 14.2 | 11.8 | 10.2 |

Again, the products according to the invention outperform conventional products with respect to early color and color-hold.

The invention claimed is:

1. A process to stabilize a polymeric resin by adding to the resin an alkaline earth metal carboxylate prepared by a process comprising the steps of
   reacting one or more alkaline earth metal oxides and/or hydroxides with a less than stoichiometric amount of a mixture of $C_4$-$C_{40}$ alk(en)yl carboxylic acids and $C_6$-$C_{30}$ alkaryl or aralkyl carboxylic acids in the presence or absence of a solvent,
   carbonating the resulting carboxylate until the base value of the product is less than 10 mg KOH/g in the presence or absence of a promoting solvent, and
   drying of the resulting product, prior, during, and/or after the carbonation step.

2. A PVC composition comprising 1-4 parts by weight, based on 100 parts by weight of resin, of a liquid stabilizer system, said stabilizer system comprising at least 5 percent by weight, but no more than 50 percent by weight of neutral carbonated alkaline earth metal carboxylate wherein the neutral carbonated alkaline earth is prepared by a process comprising the steps of
   reacting one or more alkaline earth metal oxides and/or hydroxides with a less than stoichiometric amount of a mixture of $C_4$-$C_{40}$ alk(en)yl carboxylic acids and $C_{6-30}$ alkaryl or aralkyl carboxylic acids in the presence or absence of a solvent,
   carbonating the resulting carboxylate until the base value of the product is less than 10 mg KOH/g in the presence or absence of a promoting solvent, and
   drying of the resulting product, prior, during, and/or after the carbonation step.

3. Process of claim 1 further comprising the steps of removing volatile matter and formulating the resulting product.

4. Process of claim 1, wherein the resin is PVC.

* * * * *